US 6,591,003 B2
Jul. 8, 2003

(54) OPTICAL TOMOGRAPHY OF SMALL MOVING OBJECTS USING TIME DELAY AND INTEGRATION IMAGING

(75) Inventors: Chee-Wui Chu, Fox Island, WA (US); Alan C. Nelson, Gig Harbor, WA (US)

(73) Assignee: Visiongate, Inc., Gig Harbor, WA (US)

( * ) Notice: Subject to any disclaimer, the term of this patent is extended or adjusted under 35 U.S.C. 154(b) by 0 days.

(21) Appl. No.: 10/260,908

(22) Filed: Sep. 30, 2002

(65) Prior Publication Data

US 2003/0026468 A1 Feb. 6, 2003

Related U.S. Application Data

(63) Continuation-in-part of application No. 09/927,151, filed on Aug. 10, 2001, now Pat. No. 6,522,775.
(60) Provisional application No. 60/279,244, filed on Mar. 28, 2001.

(51) Int. Cl.[7] .................................................. G06K 9/00
(52) U.S. Cl. ....................................................... 382/133
(58) Field of Search ................................. 382/131, 133; 348/295; 359/458; 250/316.1, 318, 580, 332, 370.08, 201.8, 201.9, 203.3, 559.05, 559.07, 559.15, 559.16, 206.2, 564, 208.1; 378/9, 22, 23, 25, 26

(56) References Cited

U.S. PATENT DOCUMENTS

| | | | | |
|---|---|---|---|---|
| 3,470,373 A | | 9/1969 | Brewer ..................... 250/461.2 |
| 3,497,690 A | | 2/1970 | Wheeless, Jr. ............ 250/461.2 |
| 3,657,537 A | | 4/1972 | Wheeless, Jr. ............ 250/461.2 |
| 3,833,762 A | | 9/1974 | Gudmundsen ......... 348/208.99 |
| 3,960,449 A | | 6/1976 | Carlton ....................... 356/340 |
| 3,999,047 A | | 12/1976 | Green ......................... 382/134 |
| 4,175,860 A | | 11/1979 | Bacus ........................... 356/39 |
| 4,293,221 A | | 10/1981 | Kay et al. ................... 356/318 |
| 5,141,609 A | * | 8/1992 | Sweedler et al. ........... 204/452 |
| 5,308,990 A | | 5/1994 | Takahashi et al. ........ 250/459.1 |
| 5,312,535 A | * | 5/1994 | Waska et al. ............... 204/603 |
| 5,402,460 A | | 3/1995 | Johnson ........................ 378/10 |
| 5,668,887 A | * | 9/1997 | Parker et al. ............... 382/108 |
| 5,741,411 A | * | 4/1998 | Yeung et al. ............... 204/452 |
| 5,828,408 A | * | 10/1998 | Mottin et al. ............... 348/295 |
| 5,848,123 A | | 12/1998 | Strommer .................. 378/98.8 |
| 5,987,158 A | | 11/1999 | Meyer ......................... 382/133 |
| 6,005,617 A | * | 12/1999 | Shimamoto et al. ........ 348/295 |
| 6,026,174 A | | 2/2000 | Palcic ......................... 382/133 |
| 6,165,734 A | | 12/2000 | Garini ....................... 435/7.21 |
| 6,201,628 B1 | | 3/2001 | Basiji ......................... 359/212 |
| 6,211,955 B1 | | 4/2001 | Basiji ......................... 396/326 |
| 6,248,988 B1 | * | 6/2001 | Krantz .................... 250/201.3 |
| 6,249,341 B1 | | 6/2001 | Basiji ........................... 356/73 |
| 6,251,586 B1 | | 6/2001 | Mulshine ....................... 435/6 |
| 6,251,615 B1 | | 6/2001 | Oberhardt ................. 435/7.21 |
| 6,252,979 B1 | | 6/2001 | Lee ............................. 382/133 |
| 2001/0012069 A1 | * | 8/2001 | Derndinger et al. ........ 348/295 |
| 2002/0161534 A1 | * | 10/2002 | Adler et al. ................... 702/35 |

OTHER PUBLICATIONS

Ong. SH, Development of an imaging flow cytometer. Anal Quant Cytol Histol 9(5)pp. 375–382, 1987.
Gilbert, P, "Iterative Methods for the Three dimensional Reconstruction of an Object from Projections," Journal of Theoretical Biology 36pp. 105–117, 1972.

(List continued on next page.)

Primary Examiner—Andrew W. Johns
Assistant Examiner—Shervin Nakhjavan
(74) Attorney, Agent, or Firm—George A. Leone

(57) ABSTRACT

Three dimensional reconstruction of an object of interest moving at a constant velocity. The object of interest is centered. The object of interest is imaged with optical point sources located at multiple projection angles around the object of interest, in cooperation with opposing time delay and integration (TDI) image sensors located at a distance from the objects of interest such that there is no focal plane within the objects of interest during imaging. Each of the TDI sensors has a line transfer rate synchronized to the constant velocity of the objects of interest.

20 Claims, 5 Drawing Sheets

OTHER PUBLICATIONS

Oppenheim, BE, "More Accurate Algorithms for Iterative 3 dimensional Reconstruction," IEEE Transactions on Nuclear Science NS–21 pp. 72–77, 1974.

Singer, JR, Grunbaum, FA, Kohn, P, and Zubelli, JP, "Image Reconstruction of the Interior of Bodies that Diffuse Radiation," Science 248(4958)pp. 990–993, 1990.

Mueller, K and Yage, R, "Rapid 3–D Cone–beam Reconstruction with the Simultaneous Algebraic Reconstruction Technique (SART) Using 2–D Texture Mapping Hardware", IEEE Transactions on Medical imaging 19(12)pp. 1227–1237, 2001.

Bellman, SH, Bender, R, Gordon, R, and Rowe, JE, "ART is Science being A Defense of Algebraic Reconstruction Techniques for Three dimensional Electron Microscopy," Journal of Theoretical Biology 32pp. 205–216, 1971.

Manglos, SH, Jaszcak, RJ, and Floyd, CE, "Maximum Likelihood Reconstruction for Cone Beam SPECT: Development and Initial Tests," Physics in Medicine and Biology 34(12)pp. 1947–1957, 1989, #1382.

Manglos, SH, Gagne, GM, Krol A, Thomas, FD, and Narayanaswamy, R, "Transmission Maximum–likelihood Reconstruction with Ordered Subsets for Cone Beam CT", Physics in Medicine and Biology 40(7)pp. 1225–1241, 1995, #4389.

Hampel, U and Freyer, R, "Fast Image Reconstruction for Optical Absorption Tomography in Media with Radially Symmetric Boundaries", Medical Physics 25 (1)pp. 92–101, 1998.

Jiang, H, Paulsen, KD, and Osterberg, UL, "Frequency–domain Near–infrared Photo Diffusion Imaging: Initial Evaluation in Multitarget Tissuelike Phantoms", Medical Physics 25(2)pp. 183–193, 1998.

Herman, G, *Image Reconstruction from Projections: The Fundamentals of Computerized Tomography*, Academic Press, New York, 1980.

Paulsen, KD and Jiang, H, "Spatially Varying Optical Property Reconstruction Using a Finite Element Diffusion Equation Approximation", Medical Physics 22(691–701) 1995.

Farichild Imaging, Preliminary Data Sheet CCD525, TDI, Time Delay and Integration Sensor, Jan. 12, 2001.

Farichild Imaging, Preliminary Data Sheet CCD582, TDI, Time Delay and Integration Sensor, Jan. 18, 2000.

Shapiro, HM, *Practical Flow Cytometry*, $3^{rd}$ ed., Wiley–Liss, 1995.

Bayat, S, Le Duc, G, Porra, L, Berrruyer, G, Nemoz, C, Monfraix, S, Fiedler, S, Thomlinson, W, Suortti, P, Standertskjold–Nordenstam, CG, and Sovijarvi, ARA, "Quantitative Functional Lung Imaging with Synchrotron Radiation Using Inhaled Xenon as Contrast Agent", Physics in Medicine and Biology 46(3287–3299) 2001.

Bentley, MD, Ortiz, MC, Ritman, EL, and Romero, JC, "The Use of Microcomputed Tomography to Study Microvasculature in Small Rodents", American Journal of Physiology (Regulatory Integrative Comp Physiol) 282(R1267–R1279) 2002.

Cheng, PC, Lin, TH, Wang, G, Shinozaki, DM, Kim HG, and Newberry, SP, "Review on the Development of Cone–beam X–ray Microtomography", Proceedings of the X–ray Optics and Microanalysis 1992, Institute of Physics Ser. No. 130, Kenway, PB, et al. (eds.), Manchester, UK, Aug. 31–Sep. 4, 1992, pp. 559–566.

Defrise, M, Clack, R, and Townsend, DW, "Image Reconstruction from Truncated, Two–dimensional, Parallel Projections", Inverse Problems 11 (287–313) 1995.

Defrise, M, Noo, F, and Kudo, H, "A Solution to the Long–object Problem in Helical Cone–beam Tomography", Physics in Medicine and Biology 45(623–643) 2000.

Endo, M, Tsunoo, T, Nakamori, N, and Yoshida, K, "Effect of Scattered Radiation on Image Noise in Cone Beam CT", Medical Physics 28(4) (469–474) 2001.

Jorgensen, SM, Demirkaya, O, and Ritman, EL, "Three Dimensional Imaging of Vasculature and Parenchyma in Intact Rodent Organs with X–ray Micro–CT", Am. J. Physiology 275(Heart Circ. Physiol. 44) pp. H1103–1114, 1998.

Kinney, JH, Johnson, QC, Saroyan, RA, Nichols, MC, Bonse, U, Nusshardt, R, and Pahl, R, "Energy–modulated X–ray Microtomography", Rev. Sci. Instrum. 59(1)pp. 196–197, 1988.

Kinney, JH and Nichols, MC, "X–ray Tomographic Microscopy (XTM) Using Synchrotron Ratiation", Annu. Rev. Mater. Sci. 22pp. 121–152, 1992.

Taguchi, K and Aradate, H, "Algorithm for Image Reconstruction in Multi–slice Helical CT", Medical Physics 25(4) pp. 550–561, 1998.

Yu, DF, Fessler, JA, and Ficaro, EP, "Maximum–Likelihood Transmission Image Reconstruction for Overlapping Transmission Beams", IEEE Transactions on Medical Imaging 19(11)pp. 1094–1105, 2000.

\* cited by examiner

OPTICAL TOMOGRAPHY OF SMALL MOVING OBJECTS USING TIME DELAY AND INTEGRATION IMAGING

RELATED APPLICATION

This application is a continuation-in-part of U.S. application Ser. No. 09/927,151 of Alan C. Nelson, filed Aug. 10, 2001, now U.S. Pat. No. 6,522,775 that is in turn related to co-pending provisional application of Alan C. Nelson, Serial No. 60/279,244, filed Mar. 28, 2001, both entitled "APPARATUS AND METHOD FOR IMAGING SMALL OBJECTS IN A FLOW STREAM USING OPTICAL TOMOGRAPHY."

FIELD OF THE INVENTION

The present invention relates to optical tomographic imaging systems in general, and, more particularly, optical tomography where objects are imaged using optical tomography and time delay and integration.

BACKGROUND OF THE INVENTION

U.S. application Ser. No. 10/126,026 of Alan Nelson, filed Apr. 19, 2002, entitled "VARIABLE-MOTION OPTICAL TOMOGRAPHY OF SMALL OBJECTS" is incorporated herein by this reference. In Nelson, projection images of shadowgrams are digitally captured by means of conventional CCD or CMOS image detectors. In imaging moving objects, such image sensors require short exposures to "stop motion" in order to reduce motion blur. Short exposures limit the signal to noise ratio that can be attained when imaging moving objects.

It is advantageous in optical tomography (OT) to image moving objects such as in a flow stream or entrained in a rigid medium for high throughput analysis. Additionally, in the case of objects entrained in a rigid medium, design of the presentation stage or sample positioner is simpler for constant velocity motion than for rapid stop and go motion. Moreover, in such a system, constant motion produces less vibration than stop and go motion.

Generally, time delay and integration (TDI) imaging is based on the concept of accumulating multiple exposures of the same moving object, thereby effectively increasing the integration time available to collect incident light. The object motion must be synchronized with the exposures to ensure a crisp image. Typically, TDI detectors include pixels arranged in rows and columns. An electronic signal is moved from row to row in synchrony with a moving image projected onto the device. The synchronized signal results in an extended integration time without blurring.

U.S. Pat. No. 6,249,341 to Basiji, et al. issued Jun. 19, 2001 entitled "Imaging and Analyzing Parameters of Small Moving Objects Such as Cells," discloses an apparatus where light from an object such as a cell moving through an imaging system is collected and dispersed so that it can be imaged onto a time delay and integration (TDI) detector. Basiji, et al. define a TDI detector as any pixellated device in which the signal produced in response to radiation directed at the device can be caused to move in a controlled fashion. Basiji, et al. does not address optical tomography, a deficiency overcome by the present invention.

SUMMARY OF THE INVENTION

The present invention provides an apparatus and method for three dimensional (3D) reconstruction of an object of interest moving at a constant velocity. The object of interest is centered. The object of interest is imaged with optical point sources located at multiple projection angles around the object of interest, in cooperation with opposing time delay and integration (TDI) image sensors located at a distance from the objects of interest such that there is no focal plane within the objects of interest during imaging. Each of the TDI sensors has a line transfer rate synchronized to the constant velocity of the objects of interest.

In one aspect, the present invention provides a method for three dimensional (3D) reconstruction of objects of interest in a laminar flow stream. Objects of interest are injected into a laminar flow stream such that objects are centered in the laminar flow stream and moving at a constant velocity. The objects of interest are sampled with at least one optical point source located around the laminar flow stream, in cooperation with at least one opposing time delay and integration (TDI) image sensor located opposite the at least one optical point source at a distance from the laminar flow stream such that there is no focal plane within the objects of interest during sampling. Multiple projection angles through objects of interest are sampled as they flow between the at least one optical point source and at least one opposing TDI image sensor. At least one projection image is generated with the TDI image sensor, the line transfer rate of which is synchronized to the flow rate of the objects of interest.

In another aspect, the present invention overcomes deficiencies in the prior art by providing a method and system for three dimensional optical tomography using photon point source or parallel beam projections and time delay and integration (TDI) image sensors. More particularly, a system is provided for imaging microscopic objects, including biological cells, in a flow stream or entrained in a rigid medium using optical tomography.

It is a motivation of this invention to improve signal to noise ratio of projection images in dynamic optical tomography systems by taking advantage of the ability of TDI image sensors to track moving objects.

In another aspect the present invention takes advantage of the ability of TDI image sensors to track objects moving in the direction of charge transfer on the sensor and synchronized to the sensor's line transfer rate. In one embodiment, the present invention provides a method of capturing or digitizing projection images or shadowgrams in an optical tomography instrument with a time delay and integration (TDI) image sensor oriented such that the line transfer vector is parallel to the motion vector of the cells as they are presented to the reconstruction cylinder by either a laminar flow stream or mechanically translated under computer control.

DETAILED DESCRIPTION OF THE PREFERRED EMBODIMENTS

The invention is described herein with respect to specific examples relating to biological cells, however, it will be understood that these examples are for the purpose of illustrating the principals of the invention, and that the invention is not so limited. In one example, constructing a three dimensional distribution of optical densities within a microscopic volume enables the quantification and the determination of the location of structures, molecules or molecular probes of interest. By using tagged molecular probes, the quantity of probes that attach to specific structures in the microscopic object may be measured. For illustrative purposes, an object such as a biological cell may be labeled with at least one stain or tagged molecular probe, and the measured amount and location of this probe may yield important information about the disease state of the cell, including, but not limited to, various cancers such as lung, breast, prostate, cervical and ovarian cancers.

Figure 1:
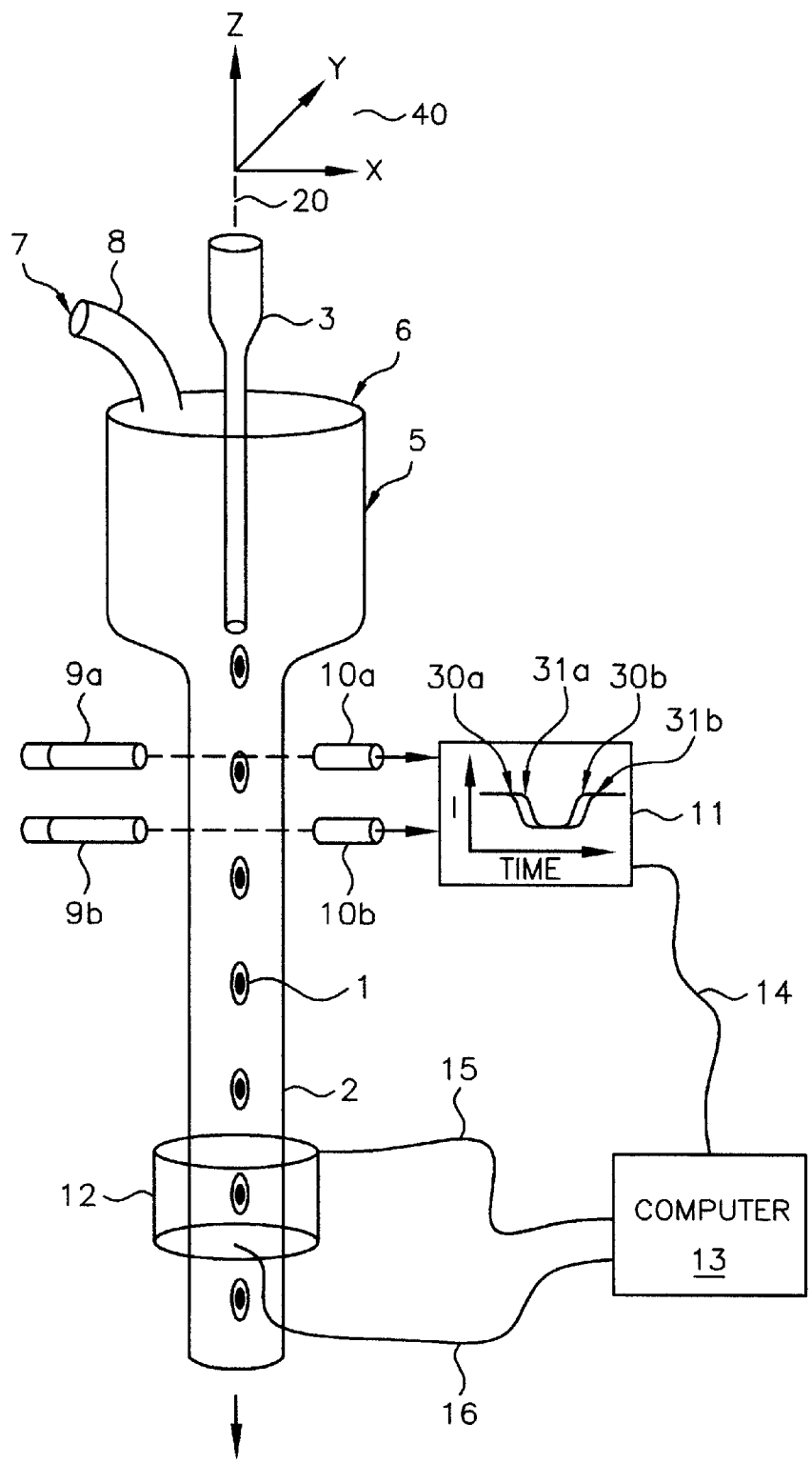
FIG. 1 schematically shows an example illustration of a Flow Optical Tomography (FOT) system as contemplated by an embodiment of the present invention.

Referring to FIG. 1, there schematically shown is an example illustration of a Flow Optical Tomography (FOT) system as contemplated by an embodiment of the present invention. The invention provides an apparatus and method for imaging small objects in a flow stream or entrained in a rigid medium using optical point source or parallel beam projections, time delay and integration (TDI) image sensors and tomographic image reconstruction. The optical tomography (OT) system includes in one example embodiment, a flow cytometer, including a reconstruction cylinder 12, positioned around capillary tube 2.

The system is oriented with reference to a coordinate system 40 having coordinates in the X, Y and Z-directions. In operation, cells 1 are injected into an injection tube 3. The capillary tube may be wider at an injection end 5 and includes a pressure cap 6. A sheath fluid 7 is introduced at tube 8 to create laminar flow within the capillary tube 2. A first source of photons 9a and a first photo detector 10a work together with a pulse height analyzer 11 to operate as a triggering device. Pulse height analyzer 11 operates to provide a first signal 30a for the beginning of a cell, and a second signal 30b for the end of the cell as it moves through the tube. The signals 30a, 30b, 31a and 31b are represented as a light intensity, "I," vs. "TIME" function within pulse height analyzer 11. The pulse height analyzer 11 generates a plurality of signals 14 that are sent to a computer 13 which, after a delay related to the velocity of the moving object and distance between the photo detector and the reconstruction cylinder 12, sends a trigger signal 15 to a reconstruction cylinder 12 to initiate and end data collection for that particular cell. Additionally, a second photon source 9b and a second photo detector 10b may advantageously be positioned at a known distance downstream from the first set such that an interval between the cell setting off a third signal 31a and setting off a fourth signal 31b may advantageously be used to calculate the velocity of the cell and also as a timing signal to synchronize a line transfer rate of a TDI image sensor. The timing signal is transmitted to computer 13 in the plurality of signals 14. The computer 13, which may be any useful personal computer or equivalent, in turn sends synchronization signals 16 to the reconstruction cylinder 12. In this way the movement of the cell along the flow axis 20 is matched by a rate of transfer of charge from one stage of the TDI sensor to the next, as described and shown in more detail below with reference to FIG. 6.

Figure 2:
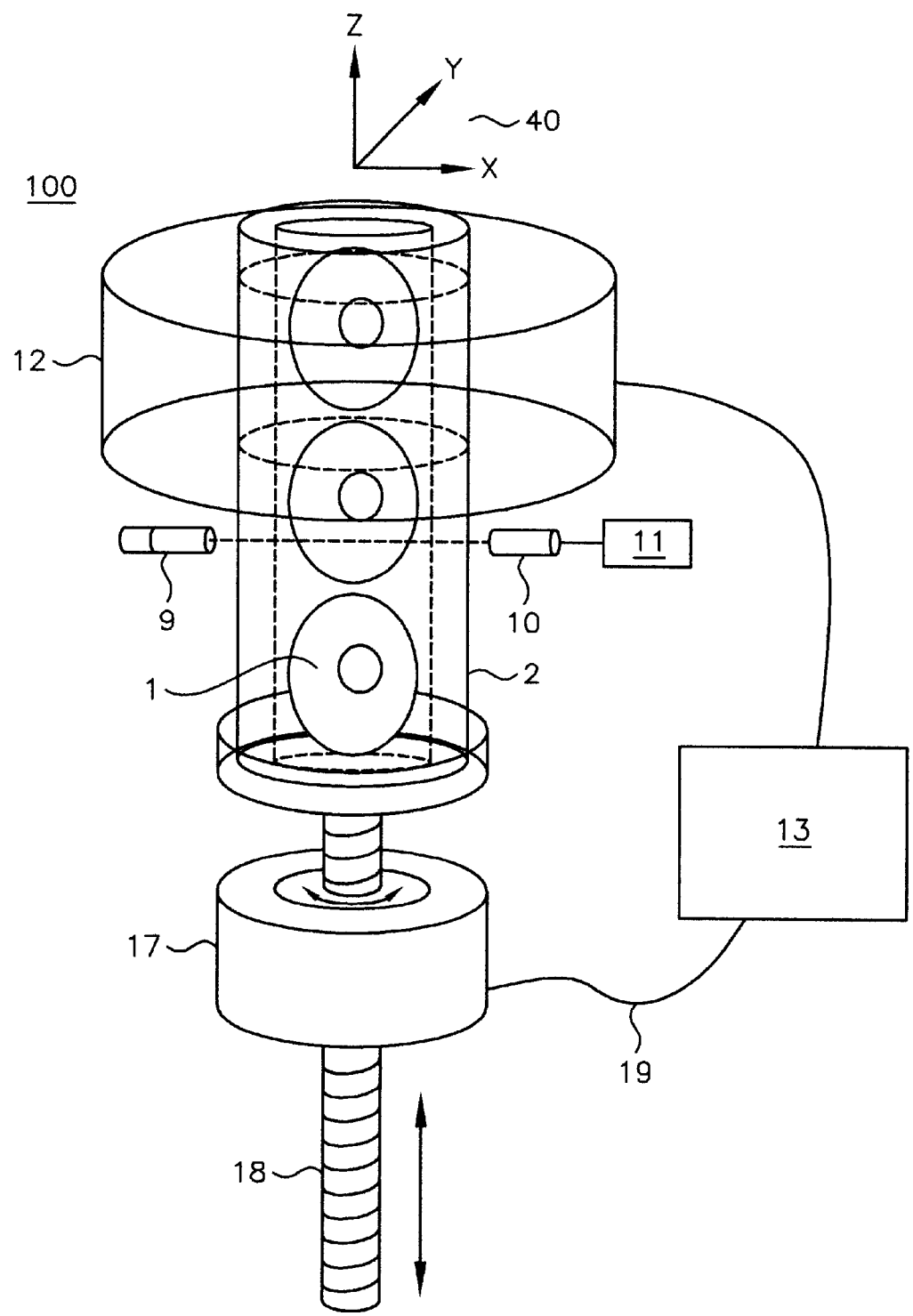
FIG. 2 schematically shows an example illustration of a Variable Motion Optical Tomography (VOT) system as contemplated by an embodiment of the present invention.

Now referring to FIG. 2, there schematically shown is an example illustration of a Variable Motion Optical Tomography (VOT) system as contemplated by an alternate embodiment of the present invention. A VOT system 100 takes advantage of a mechanical positioner to present cells entrained in a rigid medium in a tube one at a time. As compared to the FOT system described with reference to FIG. 1. in the VOT system 100 only one trigger mechanism including a photon source 9 and a photo detector 10 is required since the velocity of the cell can be precisely controlled to synchronize with the TDI sensors in the reconstruction cylinder 12. The trigger here is processed by the pulse height analyzer 11 and the computer 13 and used to start and stop data collection. As indicated by double arrow line the capillary tube in this embodiment is translated along the z-axis through the reconstruction cylinder 12 by a screw drive 18 driven by a computer controlled motor 17. The computer controlled motor 17 receives control information 19 from the computer 13. It will be understood by those skilled in the art having the benefit of this disclosure, that any mechanism capable of translating the capillary tube linearly at a constant velocity can be used in place of the screw drive.

Signals from the reconstruction cylinder may be analyzed directly or processed using computerized tomographic image reconstruction techniques to provide two dimensional or three dimensional information about cells.

Figure 3:
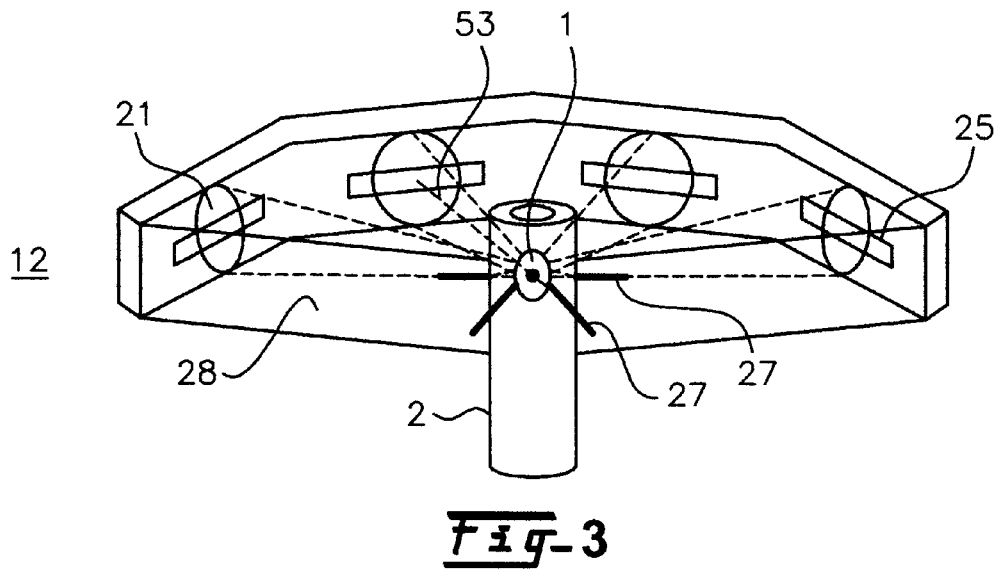
FIG. 3 schematically shows an example illustration of a reconstruction cylinder as contemplated by an embodiment of the present invention.

Referring now to FIG. 3, there schematically shown is an example illustration of a reconstruction cylinder 12 as contemplated by an embodiment of the present invention. The reconstruction cylinder 12 comprises a plurality of photon point sources 27 of selectable wavelength that are disposed around and substantially concentric with the capillary tube 2. The plurality of photon point sources 27 operate in conjunction with opposing time delay and integration (TDI) image sensors 25 that are sensitive to selectable portions of the light spectrum, where the TDI image sensors 25 are disposed to receive light from the plurality of photon point sources 27 after it has passed through the capillary tube 2, including any object such as a cell, moving within the capillary tube 2. Conventional TDI sensors, such as, for example, model number CCD525 and/or model number CCD582 available from Fairchild Imaging, Inc. of Milpitas, Calif., USA, feature integrated registers that provide signal information as an available output for processing images according to known principals. Such devices feature fast line transfer rates that can be controlled and synchronized by the user.

In operation, during the course of moving through the reconstruction cylinder, the cell 1 passes through at least one photon point source. A feature of the present invention is that a plurality of photon point sources 27 of selectable wavelength are disposed around and concentric with the capillary tube 2. The photon point sources operate in conjunction with the opposing time delay and integration (TDI) image sensors 25 that are sensitive to selectable portions of the light spectrum, thus allowing the acquisition of projections 21 of the light transmitted through the cell 1. In this manner, a set of projection rays can be generated where the projection rays can be described as the straight line connecting the source point to an individual sensing element. For illustrative purposes, one example ray is shown as ray 53. The difference between the number of photons leaving the source point along a particular projection ray and the number of photons received at the particular sensing element is related to the number of photons lost or attenuated due to interactions with the cell and other contents of the capillary tube along the projection ray path.

Note that complications may arise from light scatter, photon energy shifts, imperfect geometry and poor collimation, and photons from different sources may arrive at a particular sensing element when multiple source points are energized simultaneously. Construction of the reconstruction cylinder, for example by using the geometry for the pattern of point sources and their opposing detectors as described herein, and by proper timing or multiplexing of activation of the multiple point sources and readout of the sensor arrays, the photon contamination due to these issues can be reduced.

Photon contamination can be accounted for by calibration of the system, for example, with no cells present. That is, each light source may be illuminated in turn and its effects on each of the sensors can be measured, thereby providing offset data for use in normalizing the system. An additional calibration step may entail, for example, imaging latex polymer beads or other microspheres or oblate spheroids whose optical properties are known and span the density range of interest for cellular imaging.

FIG. 3 is a simplified schematic illustration of a particular geometry and arrangement of point sources and sensors. Only a limited number of point sources and detectors are illustrated for the sake of simplifying the drawing in order to better illustrate the principals of the invention. It will be understood by those skilled in the art having the benefit of this disclosure, that additional point sources and detectors may advantageously be packed together, and that a plurality of such units may advantageously be stacked together at predetermined radial displacements to obtain sufficient projection perspectives, for up to or exceeding 180 projections.

Figure 4:
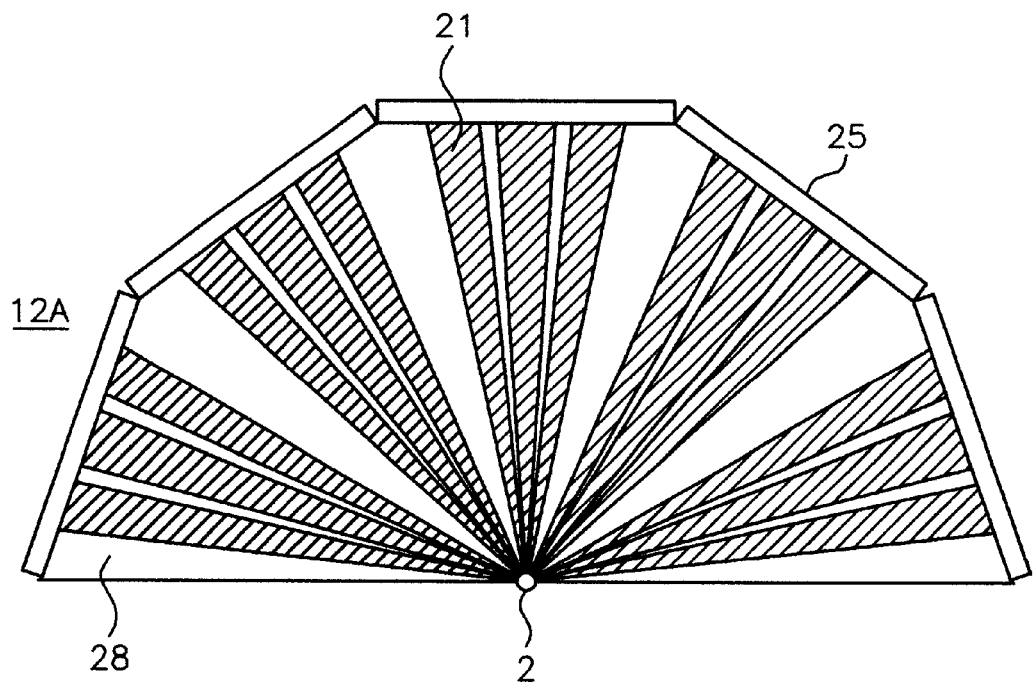
FIG. 4 schematically shows an example illustration of a partial top view of another example reconstruction cylinder.

Referring now to FIG. 4, there schematically shown is an example illustration of a partial top view of another example reconstruction cylinder 12A. Each section of the reconstruction cylinder 12A includes a TDI image sensor 25. In this example, a plurality of projections 21, here up to three projections 21, can be imaged on each sensor such that 15 projections can be accommodated in each 180 degree wide section of the reconstruction cylinder. In a preferred embodiment two such 180 degree wide sections are used. Those skilled in the art having the benefit of this disclosure will understand that substantially similar results can be achieved with many different geometries or arrangements of point sources and sensors as long as projection images of the cell are obtained from a sufficient number of radial perspectives to enable tomographic reconstruction.

Figure 5:
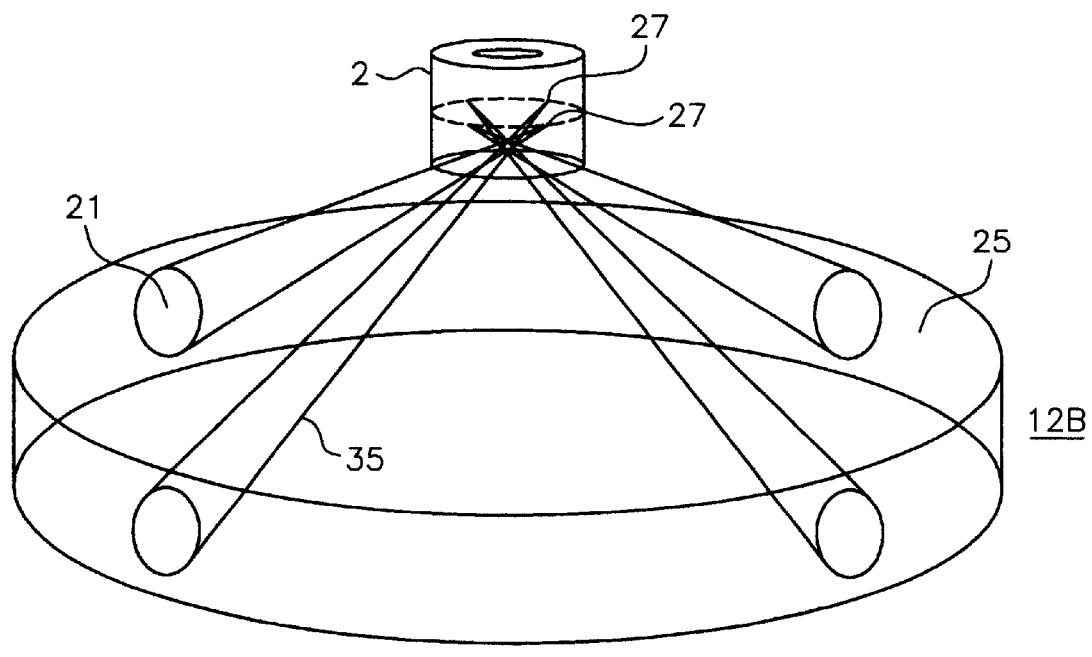
FIG. 5 schematically shows an example illustration of a reconstruction cylinder with point sources and TDI image sensors on different planes.

Referring to FIG. 5, there shown is a particularly useful design of a reconstruction cylinder 12B as contemplated by an embodiment of this invention. Here, a ring of point sources 27 is place around the capillary tube 2 and a ring of TDI image sensors 25 is placed in a plane below the point sources. While only 4 point sources are shown in the illustration, it will be understood that the ring of TDI image sensors may advantageously comprise a greater number, that being enough to enable tomographic reconstruction of images of moving objects. Further, the TDI image sensors can be below or above the plane of the point sources. The point sources may advantageously generate a cone beam 35. By placing the point sources and TDI image sensors on separate planes, point sources on opposing sides of the cylinder will not physically interfere with other projection cone beams.

The curved surface of the capillary tube 2 acts as a cylindrical lens producing a focusing effect that may not be desirable in a projection system. Those skilled in the art having the benefit of this disclosure will appreciate that the bending of photons by the capillary tube 2 can be substantially reduced if the spaces 28 between the point source and the tube and between the tube and the detector surfaces are filled with a material having an index of refraction matching that of the capillary tube. Further, the tube can be optically coupled to the space filling material. Such optical coupling may be accomplished with oil or a gel, for example.

Figure 6:
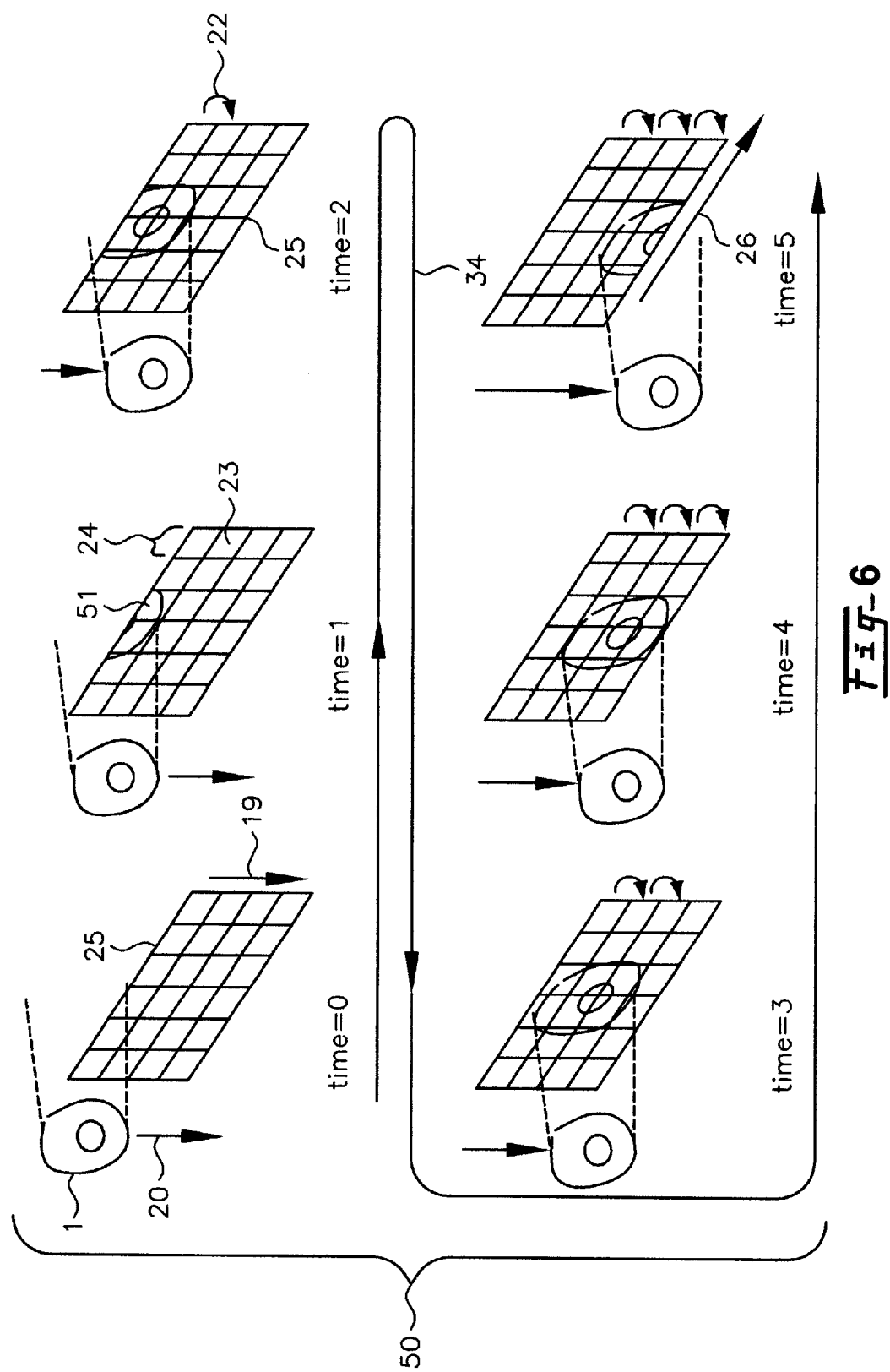
FIG. 6 schematically shows an example of a flow diagram illustrating the operation of a TDI image sensor.

Now referring to FIG. 6, there schematically shown is an example of a flow diagram 50 illustrating the operation of a TDI image sensor. Charge corresponding to an image element of the cell is transferred down a column of pixel elements 51 of the TDI sensor in synchrony with the image. The charge transfer occurs sequentially until the accumulated charge from the column is read out at the bottom register of the sensor 26.

In one embodiment of the optical tomography system contemplated by the invention, a plurality of TDI sensors 25 are oriented such that each sensor has a direction of line transfer 19 that is the same as that of cell movement 20 along the z-axis. The TDI image sensor line transfer rate is synchronized to the velocity of the cells by timing or clocking signals from the computer 13.

The process flow shows a moving cell 1 and its location with respect to a TDI sensor 25 at various times along a time line 34. At time=0 the cell 1 is just above the TDI sensor 25 and no image is sensed. At time=1 the cell 1 is partially imaged by the TDI sensor 25. A shadowgram 51 of the cell 1 is imaged one line at a time. Electrical charges 22 corresponding to each image line are transferred to the next line of sensor pixel elements 23 in synchrony with the movement of that image line down the TDI image sensor from time=0 to time=5. In this way, electrical charge corresponding to each pixel is accumulated down each column 24 of the TDI detector 25 until it is read out at the bottom register 26 at time=5.

Depending on the number of lines or stages in the TDI image sensor, the signal is boosted (e.g. up to 96 fold with a 96 stage TDI sensor such as a DALSA IL-E2 sensor available from DALSA, Waterloo, Ontario, Canada). TDI image sensors are available with up to 53 KHz line transfer rate. This is equivalent to a frame rate of 53,000 frames/sec.

Light Source.

Each light source may have the same general characteristics, preferably:

it may approximate a small circular point source, it may be bright with known spectral content, the photons emitted from the source may form a beam of a known geometry such as a cone with a small cone angle of 5 to 10 degrees or a pencil beam where all photon rays are parallel.

Each source creates data for one projection angle. A plurality of sources arranged along a helix whose axis is the center axis of the capillary tube creates data from multiple projection angles as the cell moves through the module. Depending on the sensor geometry, several point sources could be arranged co-linearly on the same circumference such that the projections do not overlap at the sensor. The desired number of sources is a function of the needed resolution within each planar reconstruction (the x-y plane) or volumetric reconstruction. Further, the wavelength of the sources is selectable either by use of various diode or other lasers or by bandpass filtering of a white or other broadband source, for example a mercury or xenon arc lamp.

There are several options that can be employed to create optical source points, such as:

an aperture in front of a laser or other high intensity photon source, an aperture utilizing surface plasmon focusing of photons on both the entry and exit sides of the pinhole, an optical fiber with a small cross-section, a short focal length lens in front of a photon source, an electron beam that irradiates a point on a phosphor surface (a form of CRT), and various combinations of the above.

The geometry using a diverging beam of light is such that, the closer the point source to the object of interest (the cell), the higher the magnification due to the wider geometric angle that is subtended by an object closer to the source. Magnification in a simple projection system is approximately M=(A+B)/A, where A is the distance between the point source and the object (cell) and B is the distance between the object and the detector. Conversely, if the required resolution is known in advance of the system design, then the geometry can be optimized for that particular resolution. For background, those skilled in the art are directed to Blass, M., editor-in-chief, *Handbook of Optics: Fiber Optics and Nonlinear Optics*, 2$^{nd}$ ed., Vol. IV, Mcgraw-Hill, 2001.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices and reconstruction algorithms, and that various modifications, both as to the equipment details and operating procedures, may be accomplished without departing from the true spirit and scope of the present invention.

What is claimed is:

1. A method for three dimensional reconstruction of objects of interest comprising the steps of:
   (a) injecting objects of interest into a laminar flow stream such that objects are centered in the laminar flow stream and moving at a constant velocity;
   (b) sampling the objects of interest with at least one optical point source located around the laminar flow stream, in cooperation with at least one opposing time delay and integration (TDI) image sensor located opposite the at least one optical point source at a distance from the laminar flow stream such that there is no focal plane within the objects of interest during sampling, and where multiple projection angles through objects of interest are sampled as they flow between the at least one optical point source and at least one opposing optical sensor; and
   (c) generating at least one projection image with the at least one TDI image sensor, the line transfer rate of which is synchronized to the flow rate of the objects of interest.

2. The method of claim 1, wherein the objects of interest comprise a cell or a cell nucleus.

3. The method of claim 1 wherein the optical projection beam is a cone beam.

4. A method for three dimensional reconstruction of objects of interest comprising the steps of:
   (a) packing objects of interest into a linear container;
   (b) sampling the objects of interest with at least one optical point source located around the linear container, in cooperation with at least one opposing time delay and integration (TDI) image sensor located opposite the at least one optical point source at a distance from the linear container such that there is no focal plane within the objects of interest during sampling, and where multiple projection angles through the objects of interest are sampled by an optical projection beam produced by the at least one optical point source as they move between at least one optical point source and at least one opposing optical sensor;
   (c) translating the linear container at a constant rate such that the objects of interest move through the optical projection beam one at a time; and
   (d) generating at least one projection image with the at least one opposing TDI image sensor, the line transfer rate of which is synchronized to the rate of translation of the object.

5. The method of claim 4, wherein the objects of interest comprise a cell or a cell nucleus.

6. The method of claim 4, wherein the step of packing objects of interest into a linear container further comprises the step of packing a plurality of cells into a tube.

7. The method of claim 4, wherein the optical projection beam is a cone beam.

8. The method of claim 4 wherein the step of sampling the objects of interest further comprises the step of imaging at least three projections onto each of the plurality of TDI sensors.

9. The method of claim 4 wherein the at least one optical point source further comprises a ring of point sources and wherein the at least one TDI sensor includes a ring of TDI image sensors placed in a plane below the ring of point sources.

10. The method of claim 4 wherein the least one optical point source is located in a reconstruction cylinder including a plurality of photon point sources of selectable wavelength that are substantially concentric and that operate in conjunction with the at least one TDI sensor, where the at least one TDI sensor is sensitive to selectable portions of the light spectrum.

11. A method for three dimensional reconstruction of objects of interest, the method comprising the steps of:
   (a) injecting objects of interest into a laminar flow stream of constant velocity; and
   (b) generating a set of projection images at a plurality of angles for at least one of the objects of interest as it flows through a reconstruction cylinder, wherein the reconstruction cylinder includes a plurality of point sources in a first plane and plurality of time delay and integration (TDI) sensors in a second plane, where the first plane and the second plane are different but parallel, and wherein the plurality of point sources and plurality of TDI sensors are arranged so as to image the objects of interest as they flow through the reconstruction cylinder.

12. The method of claim 11 wherein the reconstruction cylinder comprises more than one plane of point sources, wherein each of the more than one plane of point sources works cooperatively with each of more than one associated plane of TDI sensors to generate a plurality of images of the object of interest.

13. The method of claim 12 wherein each of the more than one plane of point sources and each of the more than one associated plane of TDI sensors are radially offset from each other to capture different perspectives.

14. A method for three dimensional reconstruction of an object of interest, the method comprising the steps of:
   (a) packing a plurality of objects into a linear container including the object of interest;

(b) centering the object of interest as necessary;

(c) translating the linear container until the object of interest is located within a reconstruction cylinder, where the reconstruction cylinder includes a plurality of point sources in a first plane and plurality of time delay and integration (TDI) sensors in a second plane, where the first plane and the second plane are different but parallel;

(d) using the plurality of point sources to illuminate the object of interest with a plurality of optical projection beams, wherein the plurality of point sources and plurality of TDI sensors are arranged so as to image the object of interest as it traverses through the reconstruction cylinder; and (e) generating a set of projection images of the object of interest at a plurality of angles.

15. The method of claim 14 wherein the plurality of point sources are located in more than one plane, and wherein each plurality of point sources in a selected plane work cooperatively with each of an associated plane of TDI sensors to generate a plurality of images of the object of interest.

16. The method of claim 15 wherein each of the plurality of point sources in a selected plane and each of the associated planes of TDI sensors are radially offset from at least one other point source plane and TDI plane respectively so as to capture different perspectives of the object of interest.

17. A method for three dimensional reconstruction of an object of interest moving at a constant velocity, the method comprising the steps of:

(a) centering the object of interest; and (b) imaging the object of interest with a plurality of optical point sources located at multiple projection angles around the object of interest, in cooperation with a plurality of opposing time delay and integration (TDI) image sensors located at a distance from the objects of interest such that there is no focal plane within the objects of interest during imaging, each of the plurality of TDI sensors having a line transfer rate synchronized to the constant velocity of the objects of interest.

18. The method of claim 17 wherein the plurality of optical point sources are located in a reconstruction cylinder including a plurality of photon point sources of selectable wavelength that are substantially concentric and that operate in conjunction with the plurality of opposing TDI image sensors, where the plurality of opposing TDI image sensors are sensitive to selectable portions of the light spectrum, and where the plurality of opposing TDI image sensors are disposed to receive light from the plurality of photon point sources after it has passed through the objects of interest.

19. The method of claim 17 wherein the plurality of optical point sources are constructed as a ring of point sources and wherein the plurality of TDI sensors include a ring of TDI image sensors placed in a plane below the ring of point sources.

20. The method of claim 17 wherein the step of imaging the object of interest further comprises the step of imaging at least three projections onto each of the plurality of TDI sensors.

* * * * *